(12) United States Patent
Tsai (10) Patent No.: US 11,890,411 B2
(45) Date of Patent: Feb. 6, 2024

(54) VENTILATOR ADAPTER AND AUXILIARY PART THEREOF

(71) Applicant: Wan-Chun Tsai, Taichung (TW)

(72) Inventor: Wan-Chun Tsai, Taichung (TW)

( * ) Notice: Subject to any disclaimer, the term of this patent is extended or adjusted under 35 U.S.C. 154(b) by 0 days.

(21) Appl. No.: 18/083,986

(22) Filed: Dec. 19, 2022

(65) Prior Publication Data

US 2023/0191046 A1 Jun. 22, 2023

(30) Foreign Application Priority Data

Dec. 22, 2021 (TW) .................................. 110148143

(51) Int. Cl.
*A61M 15/00* (2006.01)

(52) U.S. Cl.
CPC .... *A61M 15/0086* (2013.01); *A61M 15/0016* (2014.02); *A61M 15/0065* (2013.01)

(58) Field of Classification Search
CPC .......... A61M 15/0086; A61M 15/0016; A61M 15/0065; A61M 11/007; A61M 16/201; A61M 2205/6045; A61M 16/0833; A61M 16/20; A61M 16/147; A61M 16/14; A61M 15/009
USPC ............. 128/200.15, 203.23, 203.24, 207.16
See application file for complete search history.

(56) References Cited

U.S. PATENT DOCUMENTS

| | | | |
|---|---|---|---|
| 6,363,932 B1 * | 4/2002 | Forchione | A61M 15/0086 128/200.14 |
| 2010/0126502 A1 | 5/2010 | Fink et al. | |
| 2013/0081617 A1 * | 4/2013 | Cavendish | A61M 15/0068 128/203.12 |
| 2014/0360498 A1 * | 12/2014 | Alizoti | A61M 11/00 128/203.12 |
| 2016/0250437 A1 | 9/2016 | Fink et al. | |
| 2020/0129723 A1 | 4/2020 | Fink et al. | |

FOREIGN PATENT DOCUMENTS

| | | |
|---|---|---|
| CA | 2653847 C | 8/2013 |
| CN | 101745172 A | 6/2010 |
| CN | 208974878 U | 6/2019 |
| JP | 4929282 B2 | 2/2012 |
| TW | M605834 U | 12/2020 |

* cited by examiner

*Primary Examiner* — Elliot S Ruddie
(74) *Attorney, Agent, or Firm* — Best & Flanagan LLP (57) ABSTRACT

Present invention is related to a ventilator adapter and auxiliary chamber thereof. The ventilator adapter of the present invention comprises a T-shaped flow guiding adapter and an auxiliary chamber detachably connected thereto. The T-shaped flow guiding adapter contains a guiding valve that can retractably close or open its opening. The auxiliary chamber is a cylindrical hollow tubing with open ends at both sides, and a chamber partition extended into the interior of the auxiliary chamber, separating the chamber at least partially into two chambers. The present invention is able to be adapted with the conventional ventilator pipeline by using the T-shaped flow guiding adapter for connecting any suitable ventilatory medicine with the auxiliary cavity. When the ventilatory medicine is administrated, the present invention is able to guide the gas flow within the ventilator pipeline reaching into the space of the auxiliary cavity and carrying the ventilatory medicine toward the patient successfully with high amount of medicine doses for better treatment result.

2 Claims, 7 Drawing Sheets

VENTILATOR ADAPTER AND AUXILIARY PART THEREOF

FIELD OF THE INVENTION

The present invention is related to an adapter, more particularly, an adapter applicable to a ventilator.

BACKGROUND OF THE INVENTION

Respimat is a common clinical aerosol device that contains mainly long-acting bronchodilators and is administered in the form of an aerosol spray, it also is necessary to disconnect and reconnect the ventilator circuit at least two times before and after spraying.

Figure 6:
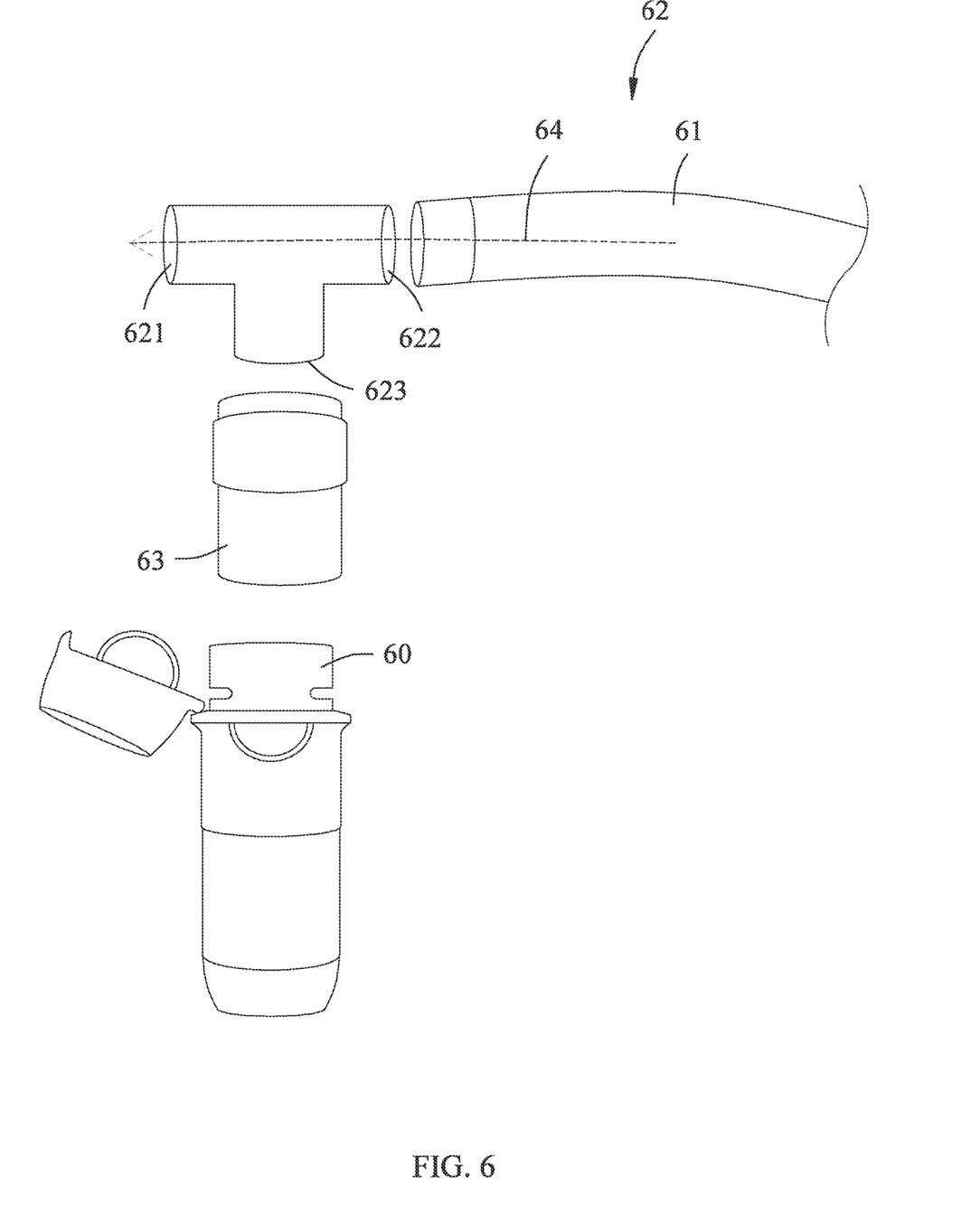
FIG. 6 is a schematic diagram of the ventilator adapter of the prior art.

As shown in HG. 6, to administer a spray solution 60, such as Respimat, a ventilator circuit 61 has to be disconnected and connected to a T-shaped tubing 62, which is a three-way tubing with a left opening 621 and a right opening 622 extending parallel to both sides of the T shape, and a vertical lower opening 623. Both ends of the disconnected ventilator circuit 61 are connected back to the left opening 621 and the right opening 622, the lower opening. 623 is connected with an adapter 63 which is adaptable to the spray solution 60 opening. For example, an airflow 64 traveling from the left to the right direction (as arrow direction in the drawing), when the medication agent contains in the spray solution 60 is pressed out, the airflow 64 will be carried along with the agent to the patient direction, to achieve the effect of ventilator administration.

However, the problem faced in actual clinical practice is that during the process of disconnecting the ventilator and reconnecting it, the moisture splashing out from the ventilator may carry infectious germs which could increase the risk of infection to the healthcare workers. Meanwhile, the ventilator circuit is exposed to the air and cannot be kept airtight, which could escalate the risk of infection to the patients. At the same time, if there is a gap at the top of the spray solution 60 as shown in FIG. 6, it will be easy to connect the spray solution 60 improperly due to the insufficient length or improper shape of the adapter 63, resulting in the leakage of the medication.

On the other hand, repeated administration causes the ventilator that has to be disconnected and connected several times, which may cause the ventilator circuit unable to maintain a seal-tightening or cause insufficient air delivery pressure, causing the dilated alveoli to collapse and to dilate again, resulting in a Shear Force Injury (SFI) and secondary damage to the alveoli.

Furthermore, since the medication agent needs to pass the adapter 63 through the spraying force of the device itself to reach the left opening 621 and the right opening 622 of the T-shaped tubing 62 before the airflow 64 can be carried to the direction of the patient smoothly, the actual situation is that most of the agent remains only in the adapter 63 and cannot be applied to the patient with an effective dose.

Even though there are conventional adapters that are suitable for the specific medication of Respimat, such as the ventilator adapter RTC 26-C on the market. However, the air tightness of this adapter is still underperformed. There still has a small airflow leaking every time when the cover is opened to receive the spray, which increases the chance of leakage of infectious germs. On the other hand, the RTC 26-C has a smaller tubing space, so the Respimat spray agent cannot be spread properly after spraying out, which reduces the absorption effect of the medication. In addition, the RTC 26-C ventilator adapter can only be used with a single Respimat spray agent, which is also relatively limited in clinical application.

Hence, it is eager to have a solution that will overcome or substantially ameliorate at least one or more of the deficiencies of a prior art, or to at least provide an alternative solution to the problems.

SUMMARY OF THE INVENTION

In order to reduce the risks to healthcare workers and patients arising from the necessity to repeatedly disconnect the ventilator during medication administration and unable to maintain a clean or airtight environment, the present invention, therefore, provides a ventilator adapter or also called a ventilator inhalation adapter that can solve the aforementioned problems.

The ventilator adapter described in the present invention comprises: a T-shaped flow guiding adapter and an auxiliary chamber detachably connected with the T-shaped flow guiding adapter, wherein: the T-shaped flow guiding adapter contains a T-shaped adapter and a guiding valve; the T-shaped adapter is a hollow tubing and contains a first opening and a second opening extending parallel to the left and right and mutually communicable with air to each other, and a third opening disposed in the vertical direction between the first opening and the second opening. The third opening at the junction between the first opening and the second opening has a tapered neck and an auxiliary chamber receiving part, the inner diameter of the auxiliary chamber receiving part is slightly larger than the size of the tapered neck, and the third opening is adapted to the guiding valve which can retractably open or close the third opening. The auxiliary chamber is a cylindrical hollow tubing and is open at both ends to receive the diverter valve fitting opening and a spraying agent fitting opening, and a chamber partition extended from the diverter valve fitting opening of the auxiliary chamber into the interior of the tubing to separate at least a portion of the interior of the auxiliary chamber into two chambers.

The present invention also provides the auxiliary chamber in the aforementioned ventilator adapter, which is a cylindrical hollow tubing and is open at both ends to receive the flow guiding valve fitting opening and a spraying agent fitting opening, and a chamber partition extended from the flow guiding valve fitting opening into the interior of the tubing to separate at least a portion of the interior of the auxiliary chamber into two chambers.

By the above description, it can be seen that the present invention has the following beneficial effects and advantages:

1. The present invention is designed with a male and female structure, using a short adapter with a flow guiding valve connected to the ventilator circuit, and then connected to another medication-inhaling auxiliary chamber when the medication is to be administered. Through the design of an air flow channel formed by the combination of the guiding valve and the spacer and the chamber partition, the air flow in the T-shaped adapter can be completely taken to the agent spraying position and be completely or almost completely carried it to the patient for inhalation to achieve a better effect of medication administration. At the same time, the design of the auxiliary chamber allows the spray agent to be appropriately spread within the chamber, which could increase the effectiveness of medication absorption, and the ventilator adapter provided by the present invention can be widely applied to various sprays, including but not limited to Respimat, MDI or SVN. When the dosing is completed, only need to disassemble the spray tank with the auxiliary chamber from the guiding valve, and a rebound mechanism will return a blocking piece of the guiding valve to its original position and close the third opening on a communicable state outwardly, and return the ventilator circuit to its original normal use state.

2. Thus, the present invention can significantly reduce the risk of infections to healthcare workers due to the splashing of moisture from the ventilator during disconnection and reconnection, which may carry infectious germs and increase the risk of infection to the patient because the tubing is exposed to air and cannot remain airtight. Also, because the airflow is successfully directed to the medication delivery end, the medication agent can be delivered completely or almost completely to the patient.

BRIEF DESCRIPTION OF THE DRAWINGS

The steps and the technical means adopted by the present invention to achieve the above and other objects can be best understood by referring to the following detailed description of the preferred embodiments and the accompanying drawings, wherein.

DESCRIPTION OF THE PREFERRED EMBODIMENTS

Reference will now be made in detail to the present preferred embodiments of the invention, examples of which are illustrated in the accompanying drawings. Wherever possible, the same reference numbers are used in the drawings and the description to refer to the same or like parts. It is not intended to limit the method by the exemplary embodiments described herein. In the following detailed description, for purposes of explanation, numerous specific details are set forth in order to attain a thorough understanding of the disclosed embodiments. It will be apparent, however, that one or more embodiments may be practiced without these specific details. As used in the description herein and throughout the claims that follow, the meaning of "a", "an", and "the" may include reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to.

Figure 1:
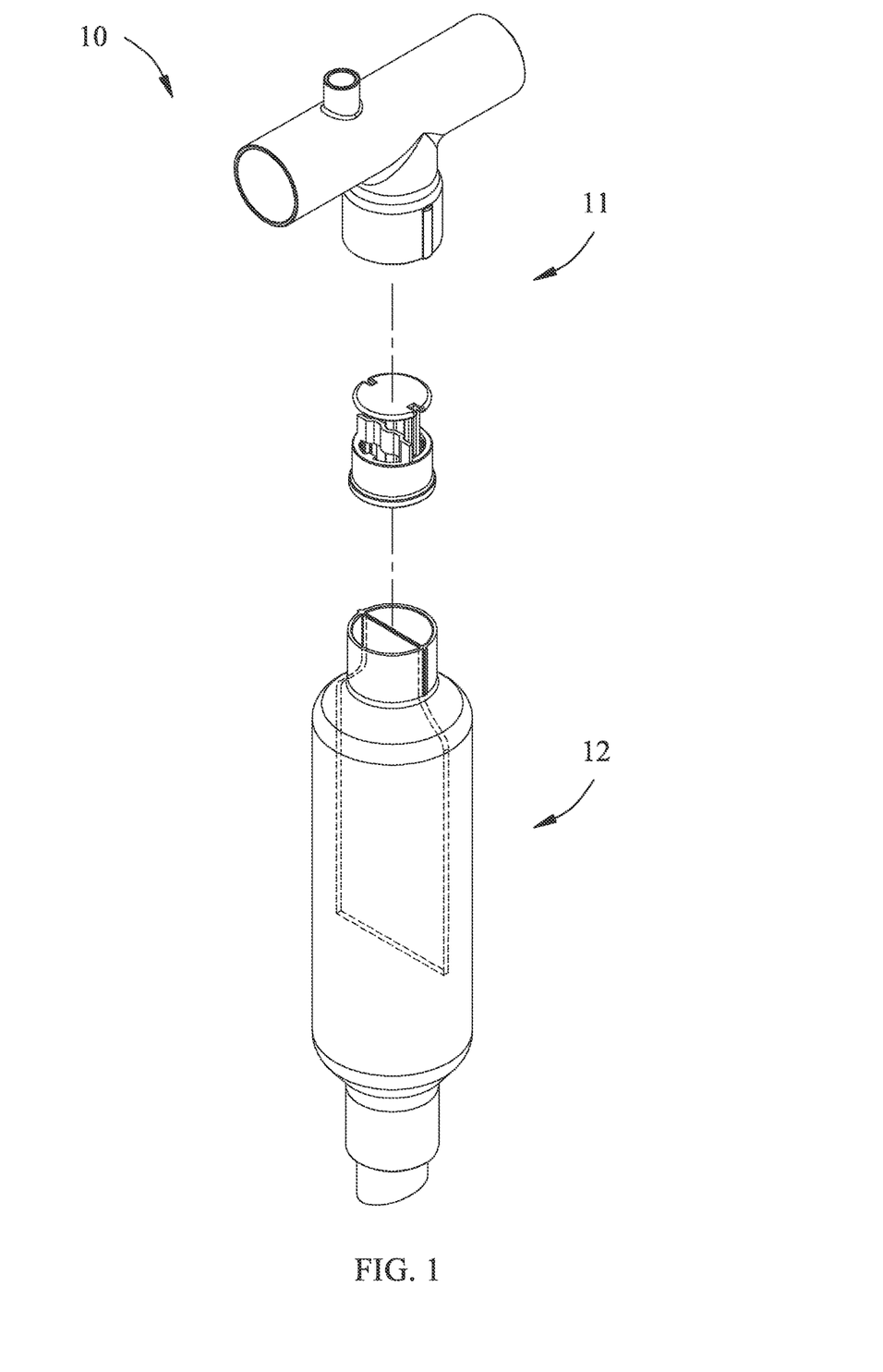
FIG. 1 is an exploded view of the ventilator adapter of the present invention.

Referring to FIG. 1, the present invention provides a ventilator adapter 10 comprising a T-shaped flow guiding adapter 11 and an auxiliary chamber 12 detachably connected to the T-shaped flow guiding adapter 11.

T-Shaped Adapter

First Preferred Embodiment

Figure 2:
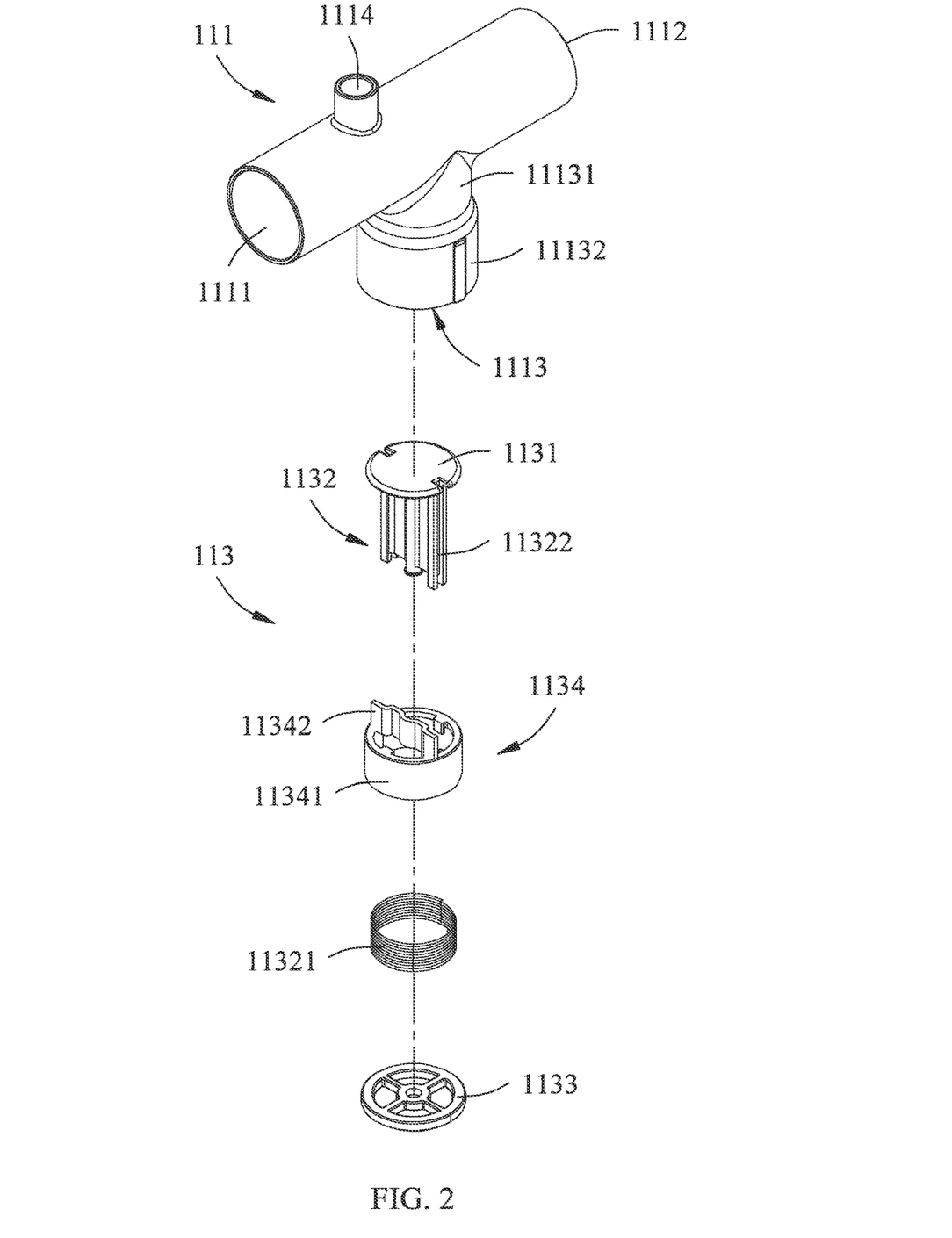
FIG. 2 is a schematic diagram of the first preferred embodiment of the T-shaped flow guiding adapter of the ventilator adapter of the present invention.

Referring to FIG. 2, a first preferred embodiment of the T-shaped flow guiding adapter 11 comprises a T-shaped adapter 111 and a guiding valve 113.

The T-shaped adapter 111 is a hollow tubing and contains a first opening 1111 and a second opening 1112 extending vertically to the left and right, and a third opening 1113 disposed in the vertical direction between the first opening 1111 and the second opening 1112. The first opening 1111, the second opening 1112, and the third opening 1113 are mutually communicable with air flow to each other.

A tapered neck 11131 and an auxiliary chamber receiving part 11132 are provided at the junction of the third opening 1113 where the first and second openings meet, the inner diameter of the auxiliary chamber receiving part 11132 is slightly larger than the tapered neck 11131, and the third opening 1113 is adapted to the guiding valve 113, which contains a blocking piece 1131, a resisting part 1133, a connecting part 1132 connected between the blocking piece 1131 and the resisting part 1133, and a stopper ring 1134 sheathed on the outside of the connecting part 1132. As shown in HG. 2, the blocking piece 1131 is sized to fit the junction opening among the third opening 1113, the first opening 1111, and the second opening 1112, preferably, the connecting part 1132 contains a rebound mechanism 11321 and a spacer 11322, the rebound mechanism 11321 could be a spring, for example, which can make the guiding valve 113 rebounds to its original position, and the spacer 11322 is in the form of a flat plate, which can temporarily separate the channel between the first opening 1111 and the second opening 1112. In this embodiment, the stopper ring 1134 is provided on the outside of the connecting part 1132, and its diameter is slightly smaller than the inner diameter of the third opening 1113, and included a ring part 11341 and a stopper piece 11342 which extends vertically upward from the top of the ring part 11341, and preferably has a suitable shape that is adapted to the connecting part 1132. When the ring part 11341 is placed on the outside of the blocking piece 1131, the stopper piece 11342 will be precisely attached to the side of the connecting part 1132. The rebound mechanism 11321 is provided within the ring part 11341 and is pushed against and limited to the stopper piece 11342 within the ring part 11341 and can be compressed and released therein.

In this preferred embodiment, the resisting part 1133 is a disc-shaped perforated body that is also suitable for the tubular channel of the third opening 1113. The resisting part 1133, when the guiding valve 113 extends to the first and second openings 1111 and 1112, can be held against the junction of the tapered neck 11131 and the auxiliary chamber receiving part 11132 to achieve the function of limiting and at the same time can compress the rebound mechanism 11321.

As also shown in FIG. 2, the T-shaped adapter 111 can be further configured with a fourth opening 1114 between the first opening 1111 and the second opening 1112 which has a suitable connector for a Metered-dose Inhaler (MDI).

Second Preferred Embodiment

Figure 3:
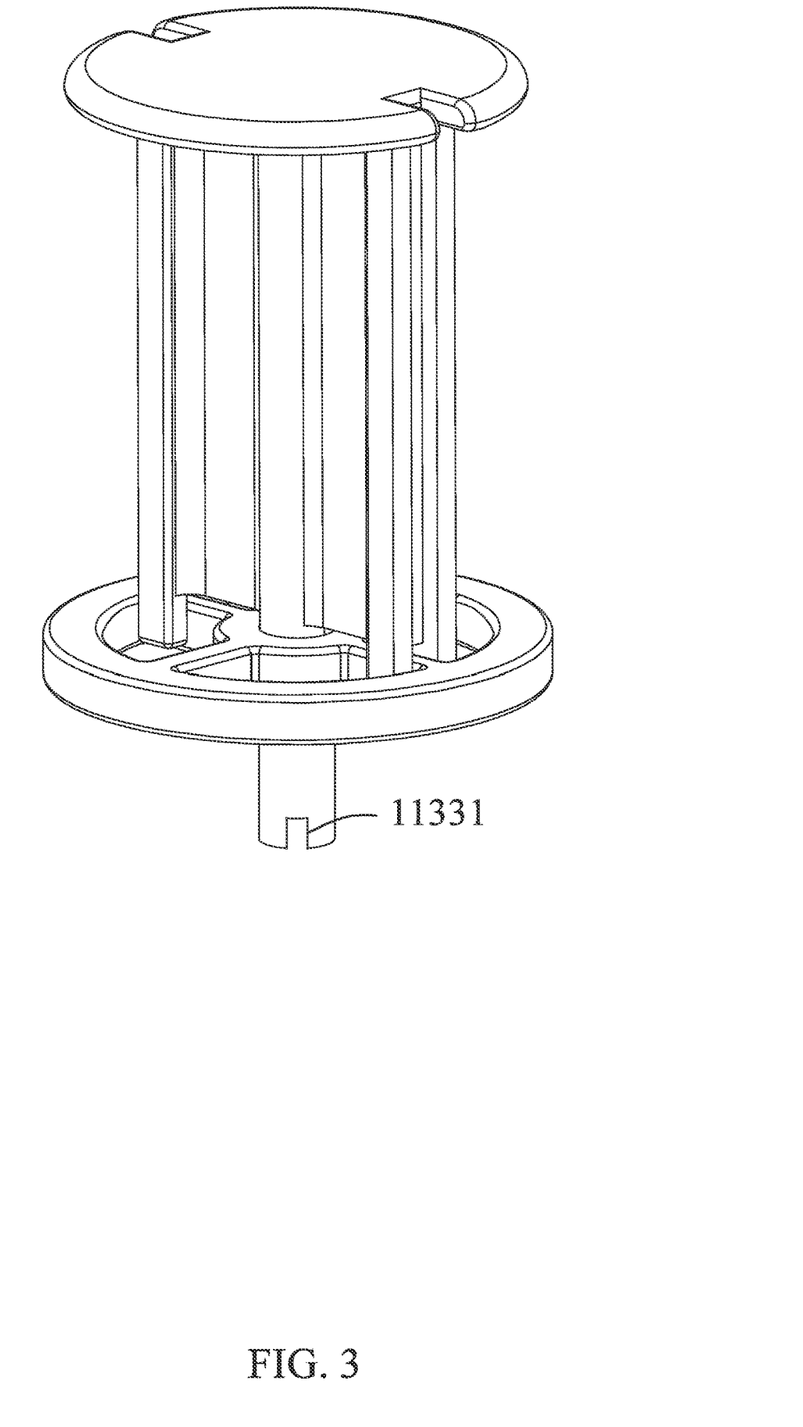
FIG. 3 is a schematic diagram of the second preferred embodiment of the T-shaped flow guiding adapter of the ventilator adapter of the present invention.

Referring to FIG. 3, the second preferred embodiment of the T-shaped adapter 111 of the present invention is basically the same as the first preferred embodiment described above, but the difference is that this second embodiment does not include a stopper ring 1134 that is disposed on the outside of the blocking piece 113 and a resisting rod 11331 is further extended from the middle of the resisting part 1133 to the outside of the third opening 1113, and the end of the resisting rod 11331 is bifurcated.

Third Preferred Embodiment

The third preferred embodiment of the T-shaped adapter 111 of the present invention is basically the same as the first preferred embodiment described above, but the difference is that this third embodiment has a magnetic attraction mechanism (not shown), such as a magnetic block in the shape of a ring, at the junction of the auxiliary chamber receiving part 11132 and the tapered neck 11131 of the third opening 1113, meanwhile, another magnetic block is set on the outside of the ring-shaped blocking piece 1131 of the guiding valve 113 for mutual attraction and fixation. Thus, this embodiment can be combined with the rebound mechanism 11321 used in the first or second embodiment, or the resisting rod 11331, when the guiding valve 113 is extended toward between the first and second openings 1111, 1112 from the third opening 1113, it is able to restore the guiding valve 113 by the magnetic attraction mechanism.

Auxiliary Chamber

First Preferred Embodiment

Figure 4A:
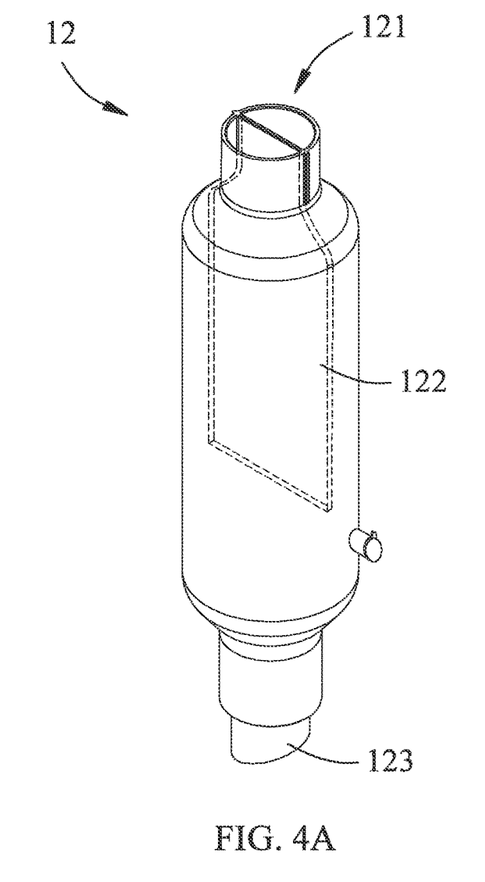
FIGS. 4A and 4B are schematic diagrams of the first and second preferred embodiments of the auxiliary chamber of the ventilator adapter of the present invention.

Referring to FIG. 4A, the auxiliary chamber 12 is a cylindrical hollow tubing and is open at both ends with a flow guiding valve fitting opening 121 at one end and a external medication fitting opening 123 at the other end.

The first preferred embodiment of the auxiliary chamber 12 is collocated with the first preferred embodiment of the aforementioned T-shaped adapter 111. A chamber partition 122 is extended from the flow guiding valve fitting opening 121 into the interior of the tubing, separating the interior of the auxiliary chamber 12 at least partially into two chambers, and the chamber partition 122 can be only partially extended inside the auxiliary chamber 12 or all extended inside the auxiliary chamber 12, the bottom of the auxiliary chamber 12 is used to accommodate any aerosol type of agent, such as Respimat, and preferably the bottom of the auxiliary chamber 12 is of sufficient length and shape to accommodate the agent, such as an oval.

Further, the side of the auxiliary chamber 12 can also be provided with an extra opening suitable for the Metered-dose inhaler (MDI) connector.

Second Preferred Embodiment

Figure 4B:
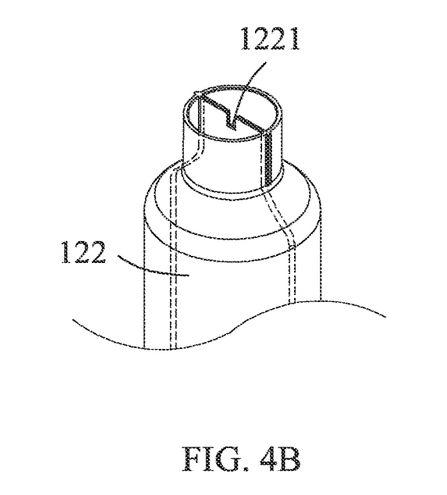

Referring to FIG. 4B, the second preferred embodiment of the auxiliary chamber 12 is collocated with the second preferred embodiment of the aforementioned T-shaped adapter 111, and further, a notch 1221 is provided at the top of the chamber partition 122 to engage with the end bifurcation of the resisting rod 11331.

Ventilator Adapter

Figure 5A:
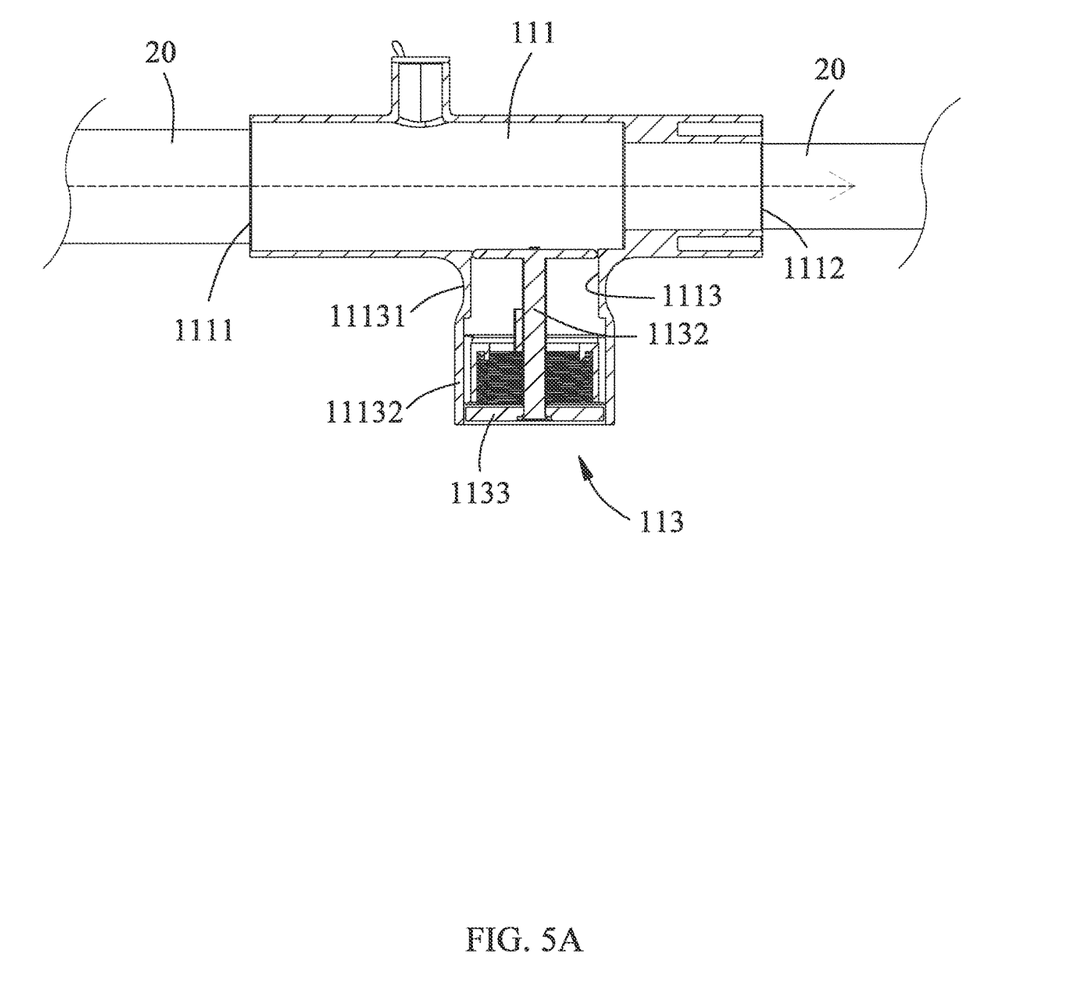
FIGS. 5A and 5B are schematic diagrams of the use process of the ventilator adapter of the present invention.
Figure 5B:
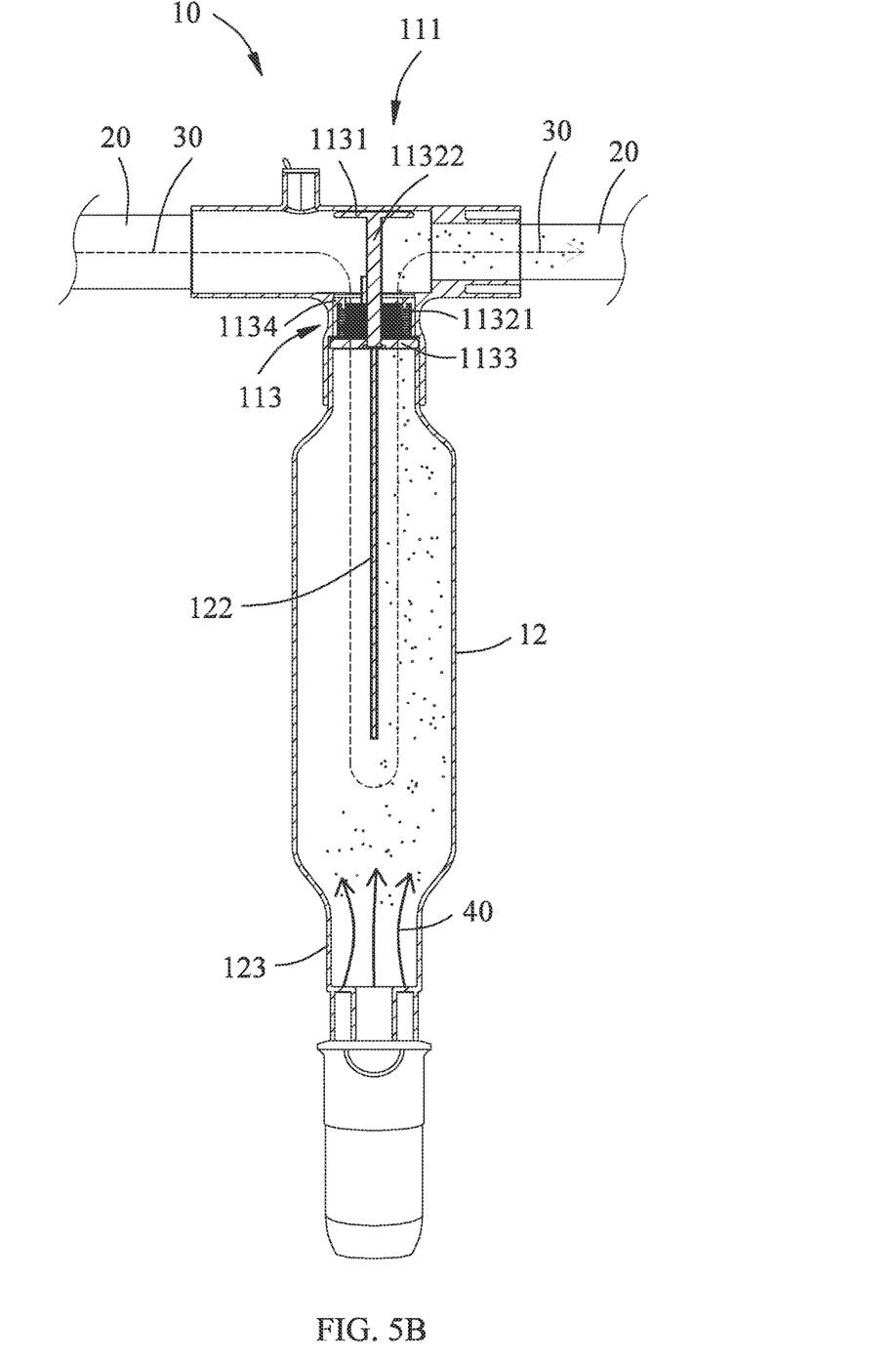

Referring to FIG. 5A and FIG. 5B, for the aforementioned first preferred embodiment example, the connection of ventilator adapter 10 of the present invention and the regular ventilator circuit 20 is mainly through the ventilator circuit 20 connecting with the first opening 1111 and the second opening 1112 of the T-shaped adapter 111 of the T-shaped flow guiding adapter 11 separately, and preferably the first opening 1111 and/or the second opening 1112 have any kind of structure that can fit the ventilator circuit 20 tightly, the present invention is not limited to it herein, only if the structure that enables the ventilator circuit 20 to fit with the first opening 1111 and the second opening 1112 with the airtight purpose is applicable to the present invention. When the T-shaped flow guiding adapter 11 of the present invention has not yet connected with the auxiliary chamber 12, the blocking piece 113 of the guiding valve 113 in the third timing 1113 maintains at the third opening 1113 junction and makes the first opening 1111 and second opening 1112 only maintain a single unobstructed channel, which is only for the air delivery under the general circumstance when the ventilator circuit 20 does not need to administer medicine.

With further reference to FIG. 5B, when the medication is to be administered, after the resisting part 1133 of the guiding valve 113 in the third opening 1113 pushed against the chamber partition 122 of the flow guiding valve opening 121 in the auxiliary chamber 12, the guiding valve 113 will be pushed against toward the space between the first opening 1111 and the second opening 1112 of the T-shaped adapter 111, and stop at the junction when the resisting part 1133 is pushed against the junction of the tapered neck 11131 and the auxiliary chamber receiving part 11132, which makes the top of the auxiliary chamber 12 is accommodated within the auxiliary chamber receiving part 11132 of the third opening 1113, and makes the rebound mechanism 11321, such as a spring, compressed at the same time. At the moment, the spacer 11322 of the guiding valve 113 and the chamber partition 122 of the auxiliary chamber 12 are engaged and form the same plane, so that the original straight channel of the ventilator circuit 20 forms a U-shaped channel toward the third opening 1113 for the airflow 30 passing through. It is worth noting that when the guiding valve 113 of the present invention is pushed against the space between the first opening. 1111 and the second opening 1112 of the T-shaped adapter 111, it may occupy ½, ⅔ or all of the space, and basically, it could achieve the claimed effect of the present invention as long as the original straight channel of the ventilator circuit 20 is formed into the U-shaped channel toward the third opening 1113. At the same time, the external medication fitting opening 123 at the bottom of the auxiliary chamber 12 can be combined with the tank of a external medication 40, the external medication 40 can preferably be Respimat, when the external medication 40 is triggered to spray in the direction of the third opening 1113, the airflow 30 will carry the external medication 40 continuously toward in the direction of the patient to achieve the effect of medication administration.

The present invention successfully enables the airflow 30 of the original T-shaped adapter 111 to completely reach the position of the spray agent 40 through the airflow channel design formed by the combination and connection of the guiding valve 113, the spacer 11322, and the chamber partition 122, and is completely or almost completely carried the external medication to the patient for inhalation to achieve a better effect of medication administration.

When the medication administration is completed, it only needs to disassemble the external medication 40 tank together with the auxiliary chamber 12 from the guiding valve 113, and the rebound mechanism 11321 will return the blocking piece 1131 of the guiding valve 113 to its original position and close the third opening 1113 on a communicable state outwardly, and return the ventilator circuit 20 to its original normal use state.

The basic mechanism of the aforementioned second preferred embodiment is the same, except that the bifurcation at the end of resisting part 1133 of the guiding valve 113 in the third opening 1113 is engaged with the notch 1221 on the chamber partition 122 of the flow guiding valve fitting opening 121 of the auxiliary chamber 12, so that the guiding valve 113 can be pushed against toward the space between the first opening 1111 and the second opening 1112 of the T-shaped adapter111, and the rebound mechanism 11321 is compressed to make the guiding valve 113 extends into the channel between the first and second openings 1111 and 1112 and to form the same airflow channel design as described above.

The above specification, examples, and data provide a complete description of the present disclosure and use of exemplary embodiments. Although various embodiments of the present disclosure have been described above with a certain degree of particularity, or with reference to one or more individual embodiments, those with ordinary skill in the art could make numerous alterations or modifications to the disclosed embodiments without departing from the spirit or scope of this disclosure.

What is claimed is:

1. A ventilator adapter comprising: a T-shaped flow guiding adapter and an auxiliary chamber detachably connected with the T-shaped flow guiding adapter, wherein: the T-shaped flow guiding adapter contains a T-shaped adapter and a guiding valve; the T-shaped adapter is a hollow tubing and contains a first opening and a second opening extending parallel to the left and right and mutually communicable with air to each other, and a third opening disposed in a vertical direction between the first opening and the second opening; the T-shaped adapter further comprises a fourth opening between the first opening and the second opening adapted for adapting a metered-dose inhaler; the hollow tubing of the T-shaped adapter forming a junction between the first opening, the second opening, and the third opening, wherein, at the third opening, the junction has a tapered neck and an auxiliary chamber receiving part, the inner diameter of the auxiliary chamber receiving part is larger than an inner diameter of the tapered neck, and the third opening is adapted with the guiding valve which can retractably open or close the third opening; the guiding valve contains a blocking piece, a resisting part, a connecting part connected between the blocking piece and the resisting part, and a stopper ring sheathed on the outside of the connecting part; the blocking piece is sized to fit in the junction, the first opening, and the second opening; the connecting part contains a spring and a spacer; the spacer is in a form of a flat plate for temporarily separating a channel between the first opening and the second opening; the stopper ring is provided on the outside of the connecting part, and a diameter of the stopper ring is smaller than an inner diameter of the third opening, and includes a ring part and a stopper piece, wherein the stopper piece extends vertically upward from a top of the ring part; and the resisting part is a disc-shaped perforated body that is configured for the third opening; the auxiliary chamber is a cylindrical hollow tubing and is open at both ends with a flow guiding valve fitting opening at a first end and an external medication fitting opening at a second end; and a chamber portion extending from the flow guiding valve fitting opening towards the external medication fitting opening to separate at least a portion of an interior of the auxiliary chamber into two chambers.

2. The ventilator adapter according to claim 1, wherein: the auxiliary chamber is provided with an opening that has a suitable connector for the metered-dose inhaler.

* * * * *